United States Patent
Postrel

(10) Patent No.: US 12,201,590 B2
(45) Date of Patent: Jan. 21, 2025

(54) EXTENDING HUMAN LIFE WITH NON-INVASIVE mTOR INHIBITOR COMPOSITIONS

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 0 days.

(21) Appl. No.: 18/236,397

(22) Filed: Aug. 21, 2023

(65) Prior Publication Data

US 2023/0404942 A1 Dec. 21, 2023

Related U.S. Application Data

(63) Continuation-in-part of application No. PCT/US2022/017142, filed on Feb. 21, 2022, and a continuation of application No. PCT/US2022/016367, filed on Feb. 14, 2022, and a continuation of application No. 17/227,320, filed on Apr. 11, 2021, now Pat. No. 12,115,135, which is a continuation-in-part of application No. 15/952,226, filed on Apr. 12, 2018, now abandoned, application No. 18/236,397 is a continuation-in-part of application No. 15/950,230, filed on Apr. 11, 2018, now Pat. No. 10,561,118, and a continuation-in-part of application No. 17/676,486, filed on Feb. 21, 2022, and a continuation-in-part of application No. 18/076,113, filed on Dec. 6, 2022.

(60) Provisional application No. 63/151,073, filed on Feb. 19, 2021.

(51) Int. Cl.
| | | |
|---|---|---|
| A61K 31/05 | (2006.01) | |
| A23K 20/111 | (2016.01) | |
| A23K 20/121 | (2016.01) | |
| A23K 20/184 | (2016.01) | |
| A61K 31/085 | (2006.01) | |
| A61K 31/192 | (2006.01) | |
| A61K 31/352 | (2006.01) | |
| A61K 31/566 | (2006.01) | |

(52) U.S. Cl.
CPC ............ *A61K 31/05* (2013.01); *A23K 20/111* (2016.05); *A23K 20/121* (2016.05); *A23K 20/184* (2016.05); *A61K 31/085* (2013.01); *A61K 31/192* (2013.01); *A61K 31/352* (2013.01); *A61K 31/566* (2013.01)

(58) Field of Classification Search
CPC .... A61K 31/05; A23K 20/184; A23K 20/168; A23K 20/121
See application file for complete search history.

(56) References Cited

U.S. PATENT DOCUMENTS

| | | | | |
|---|---|---|---|---|
| 8,221,809 | B2 * | 7/2012 | Subramanian | A23K 20/179 426/89 |
| 9,480,689 | B1 * | 11/2016 | McGlone | A61P 15/08 |
| 2018/0071314 | A1 * | 3/2018 | Dunlop | A61P 15/00 |

FOREIGN PATENT DOCUMENTS

| | | | | |
|---|---|---|---|---|
| WO | WO-2020239784 A1 * | 12/2020 | | A61K 31/05 |
| WO | WO-2022173827 A1 * | 8/2022 | | A61K 38/35 |

\* cited by examiner

*Primary Examiner* — Yvonne R Abbott-Lewis
*Assistant Examiner* — Yvonne Abbott

(57) ABSTRACT

The present invention discloses a system and method for preparing and delivering various health and longevity compositions. This invention is designed to improve the quality of life and lifespan of mammals. The compositions of the present invention are selected and designed for the purpose of efficiently delivering health and longevity enhancing therapies through oral supplementation; misting; nasal spray; intravenous, IM, and/or sub-cutaneous, injection; suppository; etc. A non-toxic therapeutic anabolic hormone replenishment is combined with rapamycin and cannabidiol. The three compounds work together to improve quality of life and healthy lifespan. Preferred additional included supplements may include metformin, growth hormone, and/or supplemented minerals. A preferred embodiment features low dose continuous supplementation, e.g., to be incorporated with a daily meal. The process of the present invention delivers an orally ingested substance, e.g., a snack, a human food supplement, an animal treat, etc., that contains the active compounds to be absorbed by the digestive system or delivered into the bloodstream.

26 Claims, No Drawings

EXTENDING HUMAN LIFE WITH NON-INVASIVE mTOR INHIBITOR COMPOSITIONS

The present application is a Continuation in Part from application Ser. Nos. 18/076,113 and 17/676,486. The applications claim priority through related applications PCT/US22/17142, Ser. Nos. 17/227,320 and 15/952,230 with priority claimed to provisional applications 62/537,027, 63/151,073 each of which is incorporated in entirety by reference.

The present invention discloses a system and method for preparing and delivering various health and longevity compositions. This invention is designed to improve the quality of life and lifespan of humans and all other mammals. The compositions of the present invention are selected and designed for the purpose of efficiently delivering health and longevity enhancing therapies through oral supplementation, misting, nasal spray, intravenous, IM and/or subcutaneous, injection, suppository, etc. A non-toxic therapeutic anabolic hormone replenishment is combined with rapamycin and cannabidiol. The three compounds work together to improve quality of life and healthy lifespan. A preferred embodiment features low dose continuous supplementation, e.g., to be incorporated with meals. The process of the present invention delivers an orally ingested substance, e.g., a snack, a food supplement, etc., that contains the active compounds to be absorbed by the digestive system or delivered into the bloodstream. Biodelivery/availability of the rapamycin and prohormone is improved using a cannabinoid substance, preferably CBD or a derivative to target delivery to intestinal mucosa and/or improve buccal uptake. (The term "food" may be used as a shorthand term for "ingestible" unless evidenced by contrary context. Terms such as therapy, device, medicament, and the like, are not in general intended to refer to actions or products that require regulatory approval, though some embodiments of the invention may require or benefit from regulatory oversight.)

The invention features one or more composite therapeutic agents in a variety of delivery formats. The invention further features therapies that incorporate such composite agents. Preferred therapy programs include a lead-in purging/cleansing phase that purges metals and reduces possible parasitic infestations. Preferably, a purging agent is introduced into the therapy recipient orally, e.g., in a pill, capsule, chewy, aqueous suspension, etc. The preferred purging agent comprises carbonized bamboo such as "Activated Carbon Tablets Charcoal Digestion Food Supplement уголь". Several vendors including, but not limited to: Bulk Supplements™ (Bulk Supplements Activated Charcoal), Swanson® (Swanson Premium Activated Charcoal Capsules), Natures Way™ (Charcoal Activated Dietary Supplement), Now® (Activated Charcoal Detox Support), etc., market similar products available in select jurisdictions. 100 to 200 mg tablets are generally sufficient. But, given the minimal toxicity of the charcoal purging agent, up to several times this amount may be administered. A flavoring or odor agent may be added to encourage intake.

As an example, a carbonized bamboo supplement is ingested in the morning with ~1% body weight water. The water intake is optional in that forced drinking is not recommended. The detox is allowed to work for a period of ~90 minutes or more to act on parasites, if any, and to absorb metals and other potentially deleterious substance. Food is withheld during this ~90 minute purge stage to allow full function of the activated charcoal unencumbered by interference from the foods. Then, in the evening, a therapeutic agent preparation is delivered. A microdosing protocol is initiated with ⅙ the FDA or other government body recommended base dose delivered over 3 to 10 hours in three or more doses separated by about at least one hour, e.g., every 2, 3, 4, or 5 hours. Protocols may be modified as directed by the practitioner to increase the amount ingested, but maintaining microdosing. For example, more than 3 doses of about ⅙ the base may be administered, preferably within a 24 hour cycle. In another example, smaller doses are administered in a number of instances to achieve the approximately ½ base dose.

Purging may be repeated on a limited scale, e.g., weekly, bi-weekly, monthly, quarterly, annually, etc. The inter-purge interval is sufficient to allow the body to return to normal digestive movement and processing.

The delivery format is at the discretion of the practitioner, though gummis have tended to be eagerly ingested by intended recipients. The preferred therapeutic includes metformin, rapamycin, growth hormone or precursor, CBD (cannabidiol), and Mg, Se, Zn, Fe, Mn, Cu, Ca, and K, supportive minerals.

For each recipient a flavor or flavors may be tested prior to therapy to determine individual preferences.

The prohormone of the composite therapeutic agent is carried by the circulatory system to its site of action where, a tissue or organ processes and/or metabolizes the prohormone to become a locally active hormone. Hormones are locally reactive when they are in contact with a receptor for that hormone. Undesired stimulation that would result from an active hormone circulating freely through multiple body tissues (as would occur when a hormone is injected) is avoided. Toxic build-up of injected hormone delivery, e.g., in the liver, kidney, adrenal gland, etc., is avoided. In accordance with the present invention, hormonal effects occur when and where needed, and toxic encounters of active hormone with tissues and cells along the circulatory pathway are avoided or at least significantly dampened.

This precursor delivery process is enhanced by formulating the food with an accessory compound that enhances controlled uptake of nutrients by the cells that line the intestines and may stimulate appetite. The present invention thus teaches the method of combining a prohormone compound with rapamycin and a cannabinoid compound, preferably cannabidiol (CBD) or a similarly acting derivative. Such similarly acting derivative may comprise a naturally occurring metabolite of CBD. The cannabinoid compound delivered in a food activates the existing cannabinoid receptors in the gut that interact with the endocrine and nervous systems to stimulate appetite and ingestion. In embodiments where CBD is jacketed around other active ingredients such as rapamycin and prohormone, preferably, dehydroepiandrosterone (DHEA). In addition to stimulating appetite and ingestion, activating these cannabinoid receptors on mucosal membranes, facilitates absorption of gut contents, including the active ingredients of the jacketed supplement, by these cells. Absorption of the rapamycin and prohormone in the food is stimulated to occur with a more rapid and more controlled delivery through buccal or mucosal cells into the bloodstream. Potential worries regarding cannabinoid effects in general circulation are minimized since the cannabinolic compounds bind to receptors on the intestinal cells and are only active there, not in general circulation. Augmenting therapeutic or food supplements may include the metformin, rapamycin, growth hormone or precursor as mentioned above. One or several supportive minerals may also be incorporated into the supplement.

As mammals and all large multi-cellular, multi-organed animals grow and develop, the maturation process is directed in essential part by hormonal communications between the animal's various systems. Different cells in the different systems respond to hormones differently depending on receptors on the cell's surface. During development and growth, the bloodstream delivers either active hormone or a precursor of a hormone that is enzymatically acted upon locally to produce the specific locally active hormone compound when needed. When the circulation delivers an injected hormone, throughout the body, the hormone will act at inappropriate sites with resultant undesired or toxic results.

Mammals are large complex organisms made of trillions of cells. The various cells differentiate to take on different tasks to support survival of the organism of which the cells are members. These cells comprise highly specialized differentiated cells and less differentiated cells that might act as stem cells to produce one or more highly specialized differentiated cell. The cells differentiate to maximize their abilities for assigned tasks while leaving other essential functions to other specialized cells. The cells specialize by emphasizing certain activities and eschewing others. They do this by selective induction of the proteins the individual cell makes and uses. We categorize cells, tissues, enzymes, etc. by assigning by designating them as belonging to one of more systems—i.e., groups interacting to perform related functions.

The digestive or gastrointestinal system is one such collaboration of specialized cells. Food (and drugs) enter through the mouth before progressing through the esophagus, stomach, small intestine and large intestine before elimination. Cells lining this system secrete substances to aid digestion including, but not limited to enzymes, acids, cofactors, bicarbonate, hormones, lubricants, water, etc. Cells along the system receive food and chemical signals from digestive cells closer to the mouth. They also are in communication with other systems in the body though hormonal and nerve signaling. Cells in the digestive system both receive and send instructions to other parts of the body to facilitate absorption and delivery of nutrients to the bloodstream and then to the whole body.

The present invention provides in oral compositions absorbable and/or metabolizable hormone supplements that can be incorporated into an animal's regular diet to invigorate metabolism and general good health. The supplemented hormone is provided in an inactive form that is available for conversion by enzymatic activity at its desired site of action to a compound that stimulates the local androgen or estrogen receptor. The prohormone delivered into the bloodstream acts as a substrate compound that individual body systems or cells can use to convert to hormones with one or more activities appropriate to that specific site. Well-known prohormones include dehydroepiandrosterone (DHEA), pregnenolone, androstenedione and androstenediol.

To deliver these prohormones as a beneficial food supplement to the cells, the digestive system plays a necessary role. Optimizing absorption timing and magnitude requires interactions between multiple body systems. As we and all mammals age these signaling pathways break down thereby reducing optimal performance, health and general well-being. Rapamycin has been shown to slow, arrest, or reverse many effects seen in aged cells. Providing supplements to replace the hormones whose production is reduced may be beneficial in itself. Rapamycin can augment these benefits. But imperfections in the intestinal uptake mechanisms reduce or skew beneficial effects, and a hormone being in a form highly active across a number of cells with receptors therefore will even in the presence of other beneficial ingredients such as rapamycin, exert undesired, potentially toxic effects.

In accordance with the present invention, absorption from the gastrointestinal tract is facilitated in both timing and magnitude by taking advantage of the body's extensive endocannabinoid receptor signaling system to efficiently and effectively deliver beneficial components where they have desired effect. In preferred embodiments a cannabinoid (preferably CBD) encasement lends mechanical and chemical durability to the microspheric particles.

Several types of cannabinoid receptors can be found in cells throughout the body. The gastrointestinal system employs several cannabinoid receptors, most commonly members of the class G-Protein-coupled Receptors (GPR or GPCR) transmembrane proteins. These receptors span 1 the plasma membrane and interact with a GTP-coupled internal protein when stimulated extracellularly. Cannabinoid receptors, $CB_1$ and $CB_2$ are two well-known members of this class. Numerous additional GPRs or GPCRs have now been shown to bind cannabinolic ligands. $GPR_{55}$ and PPARα are additional examples of endocannabinoid receptors with digestive activities. Understanding the precise mechanisms of action of cannabinoids, e.g., CBD, in the gut is not essential to enabling the present invention. CBD is known to interact in culture conditions with both the well-known $CB_1$ and $CB_2$, with a greater agonist effect on the $CB_2$ receptor. CBD, though effective at low doses appears to be well tolerated in mammals, probably in part do to its involvement in the multi-receptor cannabinoid system(s). CBD also has been shown to exhibit calming effects through at least 2 5HT receptor types. In accordance with this invention, the supplementation of CBD in the formulations with rapamycin and DHEA is the important feature. A complete understanding of the entire cascade of receptor induced interactions is not necessary for the skilled artisan and for the recipient of the formulation to benefit from the invention.

The oral composition may be orally delivered by any suitable means, including, but not limited to: as a toothpaste, a spritz, a food formulation, a food supplement, a gummie, a prescription food product, a pill, a capsule, a spray, an ampule, a chewing gum, etc. The various forms of ingestibles are included in the general reference to "pill" unless context indicates otherwise.

The invention also provides methods of making the oral composition for enhancing human animal or animal-animal interaction, or simply animal health comfort and well-being by incorporating the inactive hormone (prohormone) into one or more delivery devices.

While androgenic supplementation has been suggested and actual used as an anti-aging booster, results have been capricious with highly variable fractions of the supplement being absorbed in the intestines. While injections can overcome the gut absorption inconsistencies, constant pricking, one or more times a day—is not generally feasible. The present invention obviates the use of injections through improved and more predictable absorption and delivery of a steroid hormone precursor in conjunction with a cannabinoid component. Less psychoactive cannabinoids are preferred so that activity levels are merely increased, not greatly (and possibly unpredictably) changed. However, the doses required for enhanced uptake might be considered negligible in comparison to some of the "edibles" available in states where cannabis is legal.

The improved controlled co-delivery of rapamycin with the pro-androgenic/estrogenic stimulant to the bloodstream and deposition at desired locations in the body where local enzymes are in control for activation, decreases the potential for side-effect damage to the liver, kidneys, adrenal, and other organs or systems. Controlled uptake by the intestines minimizes the time that the gut microbiome changes the chemical makeup of the supplemented compound(s) leading to more targeted and predictable androgenic effects.

When a cannabinolic oil or alcohol is used, additional oils, including, but not limited to: vegetable, rapeseed/canola, soy, corn, peppermint, lavender, sandalwood, bergamot, rose, chamomile, ylang-ylang, tea tree, myrcene/hops, jasmine, lemon, etc. may be preferred to improve flavor, but also as a carrier for the supplemented active ingredients. The prohormone and/or cannabinolic supplement compound may be provided as an ester or other modified format to facilitate packaging, shelf-life, delivery to desired portion of the gastrointestinal tract, etc. DHEA is a prohormone for both testosterone and estrogen allowing the body's tissues to process the supplement in the tissues to outcomes specific to the organism and the tissue. DHEA has been approved by the FDA for use by humans. 7-keto-DHEA, and DHEA-S, both naturally occurring metabolites of DHEA, are alternative compounds that may substitute for DHEA or be co-administered. FDA approval is strong endorsement of the safety potential of DHEA precursor hormone.

Anabolic steroids, a class of steroids that includes androgenic compounds such as testosterone and prohormones, e.g., dehydroepiandrosterone (DHEA), pregnenolone, androstenedione, androstenediol, etc., are the steroids known for use by athletes to stimulate growth, increase strength, and allegedly improve athletic performance. These, and in fact all anabolics (steroids or other compounds binding androgen receptors and promote growth), are in a group associated with serious side effects and must be used sparingly, and most definitely not in the extreme doses used in the past by athletes. Steroid use is severely restricted in international competitions, because of the unfair increased strength with less training, but also because of the observed long-term health damage, including, but not limited to: hepatic, endocrine, and reproductive function; tumors of the liver and kidneys; cardiac abnormalities; and psychiatric symptoms. DHEA metabolism to active hormone is tissue dependent, e.g., DHEA can be converted to estrogen in appropriate tissues.

Careful and predictable controlled administration of steroid supplementation thus is a concern to pet owners who may want to enhance a pet's well-being. Cannabinoids, while themselves being banned in sports (as performance enhancing drugs), are not considered deleterious to human or animal health when cautiously administered or taken. In a legal, controlled-substance context, CBD is an especially preferred cannabinoid because it has minimal, if any intoxicating effect.

The endocannabinoid system (ECS) is an important lipid based signaling and to immunomodulator system. Lipophilic compounds, those that can readily cross plasma membranes are prime activators of these endocannabinoid pathways. Research relating to medical uses of marijuana and traditional medicines has shown that at least compounds that bind $CB_1$ and $CB_2$ participate in modulating many physiological responses including, but not limited to: appetite, respiration, metabolism, transmembrane stimulation, nutrient uptake, inflammation, allergy, pain, neurotransmission, etc. The ECS is comprised of G-protein coupled receptors (GPCRs) including, but not limited to: $CB_1$, $CB_2$, $TRPV_1$, $TRPV_2$, $TRPV_3$, $TRPV_4$, $TRPA_1$, $TRPM_8$, $GPR_{55}$, $GPR_{118}$, $GPR_{119}$, etc. and the animal homologues of human receptors of similar activity but sometimes different names. The present invention incorporates beneficial effects of cannabinoids, e.g., as provided by CBD, especially its anti-inflammatory, nutrient uptake, and metabolic enhancement effects, to stimulate and predictable control prohormone uptake by intestinal cells.

The native cannabinoid receptor ligands aka, "endocannabinoids" are classically represented by arachidonylethanolamide (anandamide, AEA) and 2-arachidonoylglycerol (2AG). Tissue levels of endocannabinoids are maintained by the balance between biosynthesis (e.g., phospholipase D and diacylglycerol lipase-dependent and other pathways), cellular uptake and degradation by enzymes principally, but not limited to: fatty acid amide hydrolase (FAAH) and/or monoacylglycerol lipases (MAGL). Since the discovery of $CB_1$ and $CB_2$ GPCRs such as $GPR_{18}$, $GPR_{55}$, $GPR_{118}$, $GPR_{119}$ and the TRPs have been recognized as members of the cannabinoid family.

Phytochemicals (substances found in plants or derivatives of the plant chemicals) or the plants themselves, have been recognized to possess biological activities in traditional medical practices. Several classes of compounds with similarities in structure and/or activities to the THC purported active ingredient of the marijuana source plant have been identified. These are available in several plants outside the *Cannabis* genus and can be, cultured (e.g., through selective breeding or genetic engineering), extracted, purified or synthesized chemically de novo or from derivatives. Such compounds including, but not limited to:

Cannabigerol class: cannabigerolic acid (CBGA) (antibiotic); cannabigerolic acid monomethylether (CBGAM); cannabigerol (CBG) (antibiotic, antifungal, anti-inflammatory, analgesic); Cannabigerol monomethylether (CBGM); cannabigerovarinic acid (CBGVA); Cannabigerovarin (CBGV).

Cannabichromene class: Cannabichromenic acid (CBCA); Cannabichromene (CBC) (antibiotic, antifungal, anti-inflammatory, analgesic); Cannabichromevarinic acid (CBCVA); Cannabichromevarin (CBCV); Cannabidiolic acid (CBDA) (antibiotic); Cannabidiol (CBD) ((antioxidant, anxiolytic, antispasmodic, anti-inflammatory, analgesic); cannabidiol monomethylether (CBDM); cannabidiol C4 (CBD-C4); cannabidivarinic acid (CBDVA); cannabidivarin (CBDV); cannabidiorcol (CBD-C1); $\Delta^9$-tetrahydrocannabinolic acid A (THCA-A); $\Delta^9$-tetrahydrocannabinolic acid B (THCA-B); 6a,10a-trans-6a,7,8,10a-tetrahydro-6,6,9-trimethyl-3-pentyl-6H-dibenzo[b,d]pyran-1-ol, ($\Delta^9$ tetrahydrocannabino-, THC) (analgesic, antioxidant, antiemetic, anti-inflammation); $\Delta^9$-tetrahydrocannabinolic acid-C4 (THCA-C4); $\Delta^9$-tetrahydrocannabinol-C4 (THC-C4); $\Delta^9$-tetrahydrocannabivarinic acid (THCVA); $\Delta^9$-tetrahydrocannabivarinic (THCV); $\Delta^7$-cis-isotetrahtydrocannabivarin; $\Delta^9$-tetrahydrocannabiorcolic acid (THCA-C1); tetrahydrocannabiorcol (THC-C1).

$\Delta^8$-tetrahydrocannabinol class: $\Delta^8$-tetrahydrocannabinolic acid ($\Delta^8$-TCA); $\Delta^8$-tetrahydrocannabinol ($\Delta^8$-THC).

Cannabicyclol class: cannabicyclol (CBL); cannabicyclolicacid (CBLA); cannabicyclovarin (CBLV).

Cannabieson class: cannabiesoic acid A (CBEA-A); cannabiesoic acid B(CBEA-B); cannabieson (CBE).

Cannabinol and cannabinodiol class: cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabinidivarin (CBDV).

Cannabitriol class: cannabitriol (CBT); 10-Ethoxy-9-hydroxy-Δ-6a-tetrahydrocannabinol (10-EHDT); 8,9-dihydroxy-delta-6a-tetrahydrocannabinol (8,9-DHDT); cannabitriolvarin (CBTV); ethoxy-cannabitriolvarin (CBTVE).

Miscellaneous class: dehydrocannabifuran (DCBF); cannabifuran (CBF); cannabichromanon (CBCN); cannabicitran (CBT); 10-oxo-Δ-6a-tetrahydrocannabinol (OTHC); $Δ^9$-cis-tetrahydrocannabinol (cis-THC); 3,4,5,6-tetrahydro-7-hydroxy-α-α-2-trimethyl-9-n-propyl-2,6-methano-2H-1-benzoxocin-5-methanol (2H-iso-HHCV); cannabiripsol (CBR); Trihydroxy-$Δ^9$-tetrahydrocannabinol (triOH-THC).

Cannabidiol is especially preferred for embodiments in the present invention for its ready availability, beneficial intestinal effects, effects after absorption through the gut mucosal cells.

LEA, PEA and OEA will bind to one or more of the endogenous cannabinoid receptors, but they are also important because they maintain AEA activity through their inhibition of the FAAH enzyme that is responsible for degrading AEA. N-alkylamides exert selective effects on the $CB_2$, and have been shown to exert anti-inflammatory effects similar to AEA. Echinacea contains multiple N-alkylamides that have mimetic effects.

Phytoalkanes, another class of chemical compounds found in various plants, also have demonstrated cannabinolic modulation traits, e.g., n-alkanes ranging from C9 to C39, 2-methyl-, 3-methyl-, and some dimethyl alkanes are common in spices such as curcumin. The major alkane present in an essential oil obtained by extraction and steam distillation was the n-C29 alkane nonacosane (55.8 and 10.7%, respectively). Other abundant alkanes were heptacosane, 2,6-dimethyltetradecane, pentacosane, hexacosane, and hentriacontane. Curcumin reduces liver fibrosis by modulating cannabinoid receptor transmission. The endo-cannabinoid system thus appears to be a highly developed multi-component integrated part of mammalian metabolisms.

Testosterone, a primary anabolic steroid, is metabolized into dihydrotestosterone in the body by the 5-α-reductase (5AR) enzyme (dihydrotestosterone is thus a metabolite of testosterone). Nandrolone is a byproduct of the aromatization (conversion) of testosterone into estrogen. Testosterone is an intermediate in natural synthesis of anabolic steroids, e.g., DHT and nandrolone. As discussed above, there are serious downsides to administering testosterone as an injected or ingested metabolic supplement.

Testosterone itself is the principal male sex hormone. Hormones are defined and classified as chemical messengers of the body, which means that hormones are what carry messages to different cells and tissues in the body to tell those cells and tissues what to do (grow muscle tissue, heal and repair, manufacture important components, perform a specific job, etc.). Without hormones of all different types, all functions within the body will proceed unregulated and out of control. How much testosterone the average male produces is dependent on many different factors, which include: individual genetics, age, lifestyle habits, nutritional habits, and activity levels. Data is most available for the human species and thus used for guidance in other mammals. On average, it has been determined that the median level of testosterone production among 30 year old human ~150-175 lb. males is between 50-70 mg weekly. Where any given individual might land within that range is dependent on the aforementioned factors. It is common knowledge that the most prominent effects of the hormone testosterone appear and are experienced during puberty, which is evidenced by an increase in testosterone production and secretion, and will typically reach the highest endogenous levels at this point in any given man's life. This significant increase in testosterone serves to impart very important physiological changes of the male body. Testosterone governs many different functions within the body. The nature of hormones in the circulation is to govern systemic functions remotely around the body, and testosterone is no exception to this. Dosing can be based on the blood levels of the intended recipient, their weight, the chemical nature of the supplement (bioavailability, half-life, partitioning in body compartments, binding to proteins, etc.) to maintain the animal at an androgen level approximating or preferably exceeding by about 1.5, 2, 2.5 or 3 times the previous average levels.

Androgens such as testosterone and DHT bind to androgen receptors (ARs) in cells. The resulting androgen-receptor complex regulates gonadotropin secretion and spermatogenesis. The androgen-receptor complex is responsible also for external virilization and for most androgen actions during sexual maturation and adult life. DHT is an especially potent androgen because it binds with greater affinity to androgen receptors than testosterone does. Testosterone production in intact mammals is stimulated by luteinizing hormone (LH). It is understood that follicle stimulating hormone (FSH) stimulates testosterone production also. Testosterone concentrations in the blood serum are regulated in part by a negative-feedback pathway in which testosterone inhibits the formation and/or secretion of luteinizing hormone-releasing hormone (LHRH). LHRH acts to stimulate secretion of LH by the pituitary gland. Testosterone acts also by regulating the sensitivity of the pituitary gland to LHRH.

Taking dogs, aka, canines, as an example, the present invention provides improved health and longevity for the animal component of the relationships humans are finding more and more significant. Maintaining a pet's well-being can support oxytocin levels in a human owner. Oxytocin is one of the natural inducers of AEA synthetic pathways. Thus, improving pet's activities that lead to oxytocin release in the human owner's body can have a beneficial side-effect of supplementing cannabinoid production and circulating levels in the human owner(s).

Humans exhibit large differences in their mitochondria and mitochondrial activities. These differences may be exacerbated with aging. By optimizing energy metabolism through monitoring and improvement in mitochondrial metabolism, (energy efficiency) the vitality effects observed through androgen balancing may be further enhanced. Accordingly, the invention may include an augmented approach wherein, in conjunction with androgen balancing as an anti-aging measure that optimizes activities and/or in conjunction with system rebalancing by enhancing cannabinoid activities, additional improvement may be obtained by also optimizing mitochondrial activity, metabolism and performance.

In a New Scientist letter by Graham Lawton: "Rapamycin is a potential anti-aging drug" (with no obviously apparent date but accessed Nov. 27, 2022), rapamycin was proposed as a potential anti-aging drug. He reported "many gerontologists see it—or similar drugs—as the best hope we have for pharmacologically slowing down the aging process."

"Rapamycin was isolated in 1972 from a bacterium found on Easter Island, aka, Rapa Nui—hence the name. For many years it was an obscure transplant drug but in the early 2000s was found to significantly extend the lifespan of worms, yeast, flies and mice. In one experiment, researchers gave rapamycin to a group of 20-month-old mice, equivalent to retirement-aged humans. They fed the mice small doses for three months, then took them off the drug and waited to for them to die. Mice usually die aged around 30 months but the drugged ones lived an extra 2 months on average. The final survivor died more than two years after the start of the experiment, at the ripe old age of 3 years and 8 months—the equivalent of around 140 in human years."

Rapamycin is a macrolide compound, a class of antibiotic that includes erythromycin, roxithromycin, azithromycin, and clarithromycin. Rapamycin's purported beneficial effects including, but not limited to: improved longevity and quality of life are not 100% understood. The bacterial derived compound is associated with improving fibroblast and mitochondrial functions as well as regulating mTOR, a highly conserved serine/threonine kinase that controls cell growth and metabolism in response to nutrients, growth factors, cellular energy, and stress.

Feeding a combination of rapamycin and DHEA thus is an underlying principle of the present invention for improving health and healthful longevity. But simple provision of these two components may not be enough. Vagaries of digestion including, but not limited to: aged cells, damaged cells, varied microbiomes, other foods and digestive stimulants cause varied, sometimes almost non-existent, beneficial outcomes from these two components. Regular co-administration, preferably jacketing, blends on DHEA and rapamycin with CBD thus provides for stably predictable lifespan enhancing effects of these three components following ingestion.

Common diseases in the aging dog include: arthritis, which reduces activity levels and may make the animal more irritable or reclusive; obesity, which can acerbate arthritis and other diseases such as cardiomyopathy and usually reduces animal activity levels; joint dysplasia, which reduces animal comfort and activity; gum disease; diabetes; blindness of various etiologies; dementia; and other diseases of aging familiar to humans. Metabolic functions may be impaired, for example, adipose tissue may experience accelerated or location improper deposition and/or aberrant utilization, glucose metabolism and metabolism of other sugars may be altered though diabetic effects and compensating metabolic shifts. Correcting mitochondrial metabolism in conjunction with safely improving androgen activities is a desired outcome for treatment or supplementation.

For example, in humans both free testosterone and total testosterone have been documented in their decline as a male ages. Up to their fifties, human males essentially maintain total testosterone with about a 25% drop in free testosterone from about the age of thirty to to about fifty. In the ensuing years both total and free testosterone continue to decline until about the age of eighty the levels are only about half the levels previous to age fifty. While there are differences in effects of aging between mammals, in general testosterone levels decline with age as the animal's vitality also declines. As an approximation, 25% supplementation may be used as augmentation beginning at approximately age 5 in dogs and age 7 in cats. The supplemented amounts will depend on the androgen compound chosen and its comparison in activity to testosterone. Advisedly testosterone levels will continue to be monitored with additional supplementation as Testosterone activity lessens.

Evidence is building that age related reduced testosterone levels in human males, and thus in other mammals, may be related to growth of pot bellies and possibly, heart attacks, strokes, osteoporosis, clinical depression and some presentations of Alzheimer's disease.

Evidence relating to human females suggests that testosterone levels may be important with regard to depression, activity level and general sense of well-being. There is also evidence that in human females, a testosterone supplement may improve activity levels and maintain a leaner body. Low testosterone levels in human females have been associated with lack of motivation and a sense of fatigue. The common weight gain and increased adipose tissue deposition in women starting approximately 10 years prior to menopause coincides with a commonly observed decreased level of circulating testosterone. This suggests an important component of the present invention relating to maintaining testosterone balance will benefit both male and female mammals.

Studies suggest that maintaining an optimized testosterone level as the animal ages can result in improved vigor, reduced injury, and greater activity and possibilities for social interaction. Testosterone is often chested as a marker for steroid hormones generally. Management of circulating testosterone also has the possible effect of preventing or reducing injury, such as muscle or joint injury, and can thereby appear as an anti-aging agent to maintain a higher level of activity. Effective supplementation in accord with the present invention should result in multiple positive effects.

While "testosterone" level management and supplementation where warranted have proved successful in improving specific health effects all over the body, administration has been carefully controlled within the medical community to avoid misuse and deleterious effects that can be associated with elevated testosterone levels that exceed safety limits.

The observation that as testosterone levels decrease during aging and that testosterone is believed to enhance muscle development suggests that the occurrences are not purely coincidence. In fact, muscle tissue expresses androgen receptor (AR) protein so it would be understood that testosterone would influence muscle metabolism. Supporting evidence that testosterone supplementation or replacement increases muscle fiber protein synthesis and that pluripotent stem cells capable of differentiating into muscle fiber cells have high levels of AR expression suggests a causal relationship exists. Accordingly, Supplementing androgen, e.g., testosterone to an aging person may maintain or build muscle mass. Better muscle mass is associated with lower incidences of diabetes so the benefits of testosterone balancing would be expected to cascade through many organs and tissues. But at lower levels of activity while testosterone balance may produce profound benefits an even greater improvement is possible if mitochondrial optimization is partnered with the balancing. Not intending to disparage the invention approach wherein animal health and relationships are augmented by testosterone balancing, the invention recognizes that the augmentation can be amplified by 1) maintaining or optimizing mitochondrial performance as part of the intervention; and/or 2) by taking advantage of cannabinoid compounds to facilitate balancing throughout additional systems. On the other hand, allowing mitochondrial impairment or other systemic imbalances to degrade benefits of androgen balance would be seen as slowing or limiting benefits of the balancing itself. In fact, relating to aging, some believe that oxidative stress of mitochondria may have a major role in age related energy deficit.

Androgenic compound abusers have contributed to testosterone's and other androgenic hormones' shocking disparagement in the news and social media through reports of occasional wild and violent activities. There are also reports of severe health outcomes such as brain tumors, to but perhaps, partly related to publicity from these warnings about androgenic misuse and exhibits of "over manliness", steroid supplementation/abuse continues in a significant segment of the population, both male and female. Though abuse may present long term problems for the individual and society, society at large, law enforcement, and politicians can understand that the abuse is a result of testosterone's positive effects.

While some desired effects, for example, increased muscle mass in body builders and other professional athletes, may be valued for their immediate effects, long term effects, for example use over decades, has been shown to increase propensity for heart attack and stroke. The length of administration and the expected remaining lifespan of the individual should be considered before enhancing androgen in the bloodstream.

Other noted effects include elevated LDL and higher LDL/HDL ratio, increased blood pressure, increased cancer, for example, brain and liver, and difficulty in movements that may be caused by excess tissue deposition. Androgen abuse is also associated with testicular wasting or atrophy which in humans may or may not be desired depending on one's desires for fatherhood. In neutered dogs, this of course would not be a relevant concern.

Most of these recognized problems can be avoided or minimized simply by managing testosterone blood levels to levels more prevalent in normal animals or limiting administration to older animals with for example an expected remaining lifespan of about a decade or less. For example, the irritability, aggressive behaviors, rage, violence, delusions, manic eating, etc., appear to be associated with abuse of androgens that involves massive dosing regimens; liver disease and tumor events appear associated with long term administration of moderate to high doses.

The present invention seeks to avoid these problems by optionally providing systems wide rebalancing tools in the form of cannabinolic augmentator supplements or facilitators, e.g., CBD, preferably as a protective coating with a prohormone such as DHEA and the bacterially derived rapamycin. The rapamycin supplement is effective at relatively low dosages, e.g., about 0.1, 0.2, 0.5, 0.75, 1, 1.5, 2 and 3 mg/kg/day. Gummies or other supplements should take into account the mass of the individual taking the preparation and the expected frequency of administration. The literature has noted effects in continuous (in culture), daily and weekly administrations. Dosages several fold greater than these have been used without serious adverse effect, e.g., in combination with cyclosporin following an organ transplant.

Restoration of testosterone (as a marker for steroid hormones) to approach normal physiological levels can help to restore to a more youthful state and improve the function of many of the different systems where testosterone's effects on the cellular level are accomplished. This includes, for example, action in the bone marrow that increases red blood cell count, which translates to increased endurance, improvement in energy, well-being, and restoration of muscle mass. Restoration of appropriate mitochondrial activity, e.g., by providing rapamycin in a useful format supports and augments the beneficial effects of restored hormone levels.

There are various studies that have determined where, on average, testosterone levels should be in males according to various age groups. Generally, testosterone in human males declines about 1% per year from the late thirties.

Supplementation in accordance with the present invention may help avoid serious medical problems. For example, osteoarthritis and hip dysplasia are especially common and problematic. Individuals will reduce activity level and avoid some previous activities to hide the symptoms or to avoid associated pain. Aging is also associated with a general lethargy that can be a result of or mask other diseases such as a failing heart, painful joints, decreased muscle tone, arthritis, etc. and may be a factor in weight gain that can cause or exacerbate other disorders. A supplement of the present invention can reduce these symptoms.

Mammalian bodies have internal means of messaging. Blood flow can be increased or decreased to an area or organ. Nerves sense what is happening at different locations within the body and then transmit information to the central nervous system where multiple inputs are analyzed and coordinated to initiate an output. The output could be neurotransmitter secretion causing a nerve impulse sending instructions to another location in the body. Another very important means of internal commutation is the endocrine system which uses hormones as signaling agents. Hormones are chemicals just as neurotransmitters, but hormones have effect distant from the place of release.

Hormones are chemical messengers used to transfer information through the bloodstream from one part of the body, generally an endocrine gland, to the body in general or to a specific target organ that has a receptor capable of binding or receiving the hormone. Target organs have specialized receptors that gather information that has been transferred from the circulatory system by hormones. An example of a target organ is the uterus, which is stimulated by the circulating hormone estrogen to develop uterine glands. Hormone production—for example, testosterone, estrogen, and progesterone—is regulated by another hormone secreting endocrine gland, the pituitary, at the base of the brain.

Prohormones are building block chemicals used to produce the resultant hormones. In general, the blood levels of sex steroid prohormones are not regulated by any one factor. They are removed from circulation when they bind one of the cells expressing their receptor protein. In contrast, prohormones are generally available to assist in the production of hormones at a site in need that is stimulated by messages in the organism to bind and activate the prohormone, which then act locally or as chemical messengers to other target organs. Injecting a functioning hormone eliminates the problem that may stem from insufficient prohormone, but undermines the natural feedback controls of the body. Increasing circulating prohormone in accord with the present invention thus can result in more balanced supplementation.

The present invention is based in part on the insight that administering one or more androgenic hormones or prohormones to generally healthy appearing individuals can increase their overall health and though not as readily observable, achieving an optimal level of circulating hormone may be associated with an increased quality of life, possibly through enhancement of the immune system's ability to defend against bacteria and viruses, to resist cancer, to enhance the circulatory system, and/or to ameliorate undesired stress-responses. Co-administration of compounds active in the cannabinolic systems especially when the cannabinoid is provided as a digestive protectant and uptake enhancer, fine-tunes and facilitates such administrations. Further improved outcomes can be provided through co-administration of a prohormone such as DHEA with rapamycin, a mitochondrial sustaining bacterial derivative, that supports metabolic activities of the hormone balanced cells.

DHEA, a compound with FDA approval for use in humans, is the preferred prohormone for inclusion in products of the present invention. DHEA, aka, androstenolone, is an endogenous steroid hormone precursor produced mostly in the adrenal glands, but also in gonads and brain tissue.

DHEA is converted to DHEA 3β-sulfate (DHEA-S) by sulfation at the C3β position by the sulfotransferases SULT2A1 and SULT1E1 DHEA-S is more stable in circulation, present in amounts perhaps 250 to 300 times DHEA. DHEA-S thus acts as a reservoir or sink for long term availability of the prohormone. DHEA-S is retro-converted back into DHEA in target peripheral tissues by steroid sulfatase. DHEA/DHEA-S is the most abundant circulating steroid measured in humans. The circulating DHEA serves as a substrate for biosynthesis of androgen and estrogen steroids in the gonads and many other tissues. Potential biological effects of DHEA are reduced by the natural conversion to DHEA-S. DHEA therefore can be fed or supplemented without serious concerns. But to reduce these negligible risks even further, DHEA-S may be incorporated in one or more products of the present invention. However, when using DHEA-S as a significant supplement, increased stimulation with a cannabinolic compound such as CBD can be essential for enhanced digestive uptake. Accordingly, formulations comprising DHEA and DHEA-S may be considered for use interchangeably.

Rapamycin, a compound derived from a bacteria harvested over a half century ago from Easter Island may also be incorporated in a supplement/medicament of the present invention. The rapamycin addend will stimulate gut health in addition to a cannabinoid such as CBD co-compounded in the formulation. These substances act in concert to increase intestinal absorption, reduce gut inflammation, improve DNA health and longevity while promoting efficient recycling of cell material through better controlled autophagy. Given the high rate of intestinal cell turnover, i.e., multiple divisions and DNA reconstruction, the combined effect of these components improves cell health and thereby increases health and well-being of the individual.

Such medicament may be formulated as a simple mixture of DHEA, CBD and rapamycin formatted as microsphere compositions bound in a gel and/or gummi format molded or extruded into a preferred shape. Many gummi preparations are known in the art and can be used to deliver microspheres of the present invention. Individual microspheres of rapamycin and DHEA may be suspended within a gummi where the gummi continuous phase comprises CBD in the bulk gummi mixture. A preferred embodiment features microspheres of rapamycin and DHEA encapsulated in a CBD coating. The CBD coating serves two purposes: 1) it maintains microspheric structure allowing for almost unlimited selection from the gummi preparations known in the art, and 2) it facilitates delivery of the microspheres intact into the small intestine where the CBD promotes intestinal activity in absorbing and processing all three main ingredients. The DHEA is efficiently absorbed and processed in the intestinal mucosa for delivery through the hepatic portal system to the liver and then throughout the body. The rapamycin acts to promote cell health and recycling first in the intestine and then liver before circulation to other body organs.

Gelatin matrices can form sugar free or low sugar product. Sugar based, corn syrup based, or other gummi preparations are also acceptable with the CBD encapsulated microspheres. Following ingestion, the CBD acts to activate or facilitate gut cells to absorb and process both rapamycin and DHEA. The rapamycin further amplifies CBD effect on gut cells resulting in improved absorption, gut health, and overall activity. An enteric encapsulation or coating can be added for better delivery to the intestinal cells. Flavoring substances are preferably added to increase appeal to the animal benefiting from the product.

The gummi can release CBD coated microspheres of rapamycin and DHEA into the saliva allowing absorption in the mouth. Microspheres may also be enteric coated to promote intact delivery into the intestine. A preferred chewing gum product features approximately one third of the rapamycin/DHEA/CBD coated microspheres without an enteric coating with about two thirds enterically coated for efficient intestinal delivery. The dual absorption modes provide benefit from direct entry into circulation from buccal absorption while also providing intestinal and hepatic benefit.

The compositions used in the present invention are preferably formulated and controllably administered to induce desired effects without also inducing undesired side effects, such as undesired anabolic or androgenic effects. The delivery of the steroid precursor with minimal activity prior to local processing concomitantly with a cannabinoid to enhance food intake and digestive uptake, and a metabolism balancing/correcting component such as rapamycin, accomplishes these goals.

Dose will depend on the initial status of circulating hormone, on the active ingredient and its activity, on the size of the individual, the frequency of dosing and the rate at of metabolizing the active ingredient(s) of the composition. Thus suitable unit doses may range from about: 0.01 mg to 500 mg, e.g., 0.01 mg, 0.05 mg, 0.07 mg, 0.1 mg, 0.15 mg, 0.2 mg. 0.5 mg, 1.0 mg, 2 mg, 3 mg, 5 mg, 7 mg, 10 mg, 20 mg, 25 mg, 30 mg, 50 mg, 75 mg, 100 mg, 120 mg, 150 mg, 175 mg, 200 mg, 250 mg, 300 mg, 350 mg, 400 mg, 450 mg, or 500 mg. Depending on the route of delivery, the animal's size, the animal's age, the animal's gender, the specific composition, etc. other ranges may be relevant, for example, 10 mg-200 mg, 12.5 mg to 150 mg, 15 mg-100 mg, 20 mg-75 mg, 20 mg-50 mg, or 50 mg-100 mg, etc. Dosages in amounts of about 0.1, 0.15, 0.2, 0.3, 0.5, 1, 2, up to 5 mg/day may be administered. Dosing in the lower ranging is preferred, but in cases with serious estrogen or androgen deficits dosing in the higher ranges may exhibit greater benefit.

Salts, esters, metabolites, protein bound, glycosylated, or matrixed formats of delivery a can be used in the composition, provided they are converted in vitro or in vivo to an active form. Accordingly, the compositions of the invention may comprise pro-hormone that is bound, covalently or non-covalently to a non-hormonal substance and/or jacketed in an oily wax such as CBD.

The compositions, especially when provided as a food, may optionally include additional vitamins or minerals and scents or flavorings or flavor enhancers to render the composition more acceptable A protein binder and/or a vitamin such as one of the B vitamins, e.g., B6 might be added as it or they might be found to help stabilize hormone level. Magnesium, selenium, lithium, potassium, iron, phosphorus, zinc, manganese, etc. Vitamins A, B, C, D, and K, including, but not limited to: A, B, C, D, K, etc., such as B1 thiamin, B2 riboflavin, B3 niacin, B5 panthenic acid, B6, pyridoxal, B7 biotin, B9 folic acid/folate, B12 cobalamin, C ascorbate/ascorbic acid, D2 ergocalciferol, D3 cholcalciferol, retinol, retinyl ester, vitamin A carotenoids, K1 phylloquinone, K2 menaquinone, etc.

While these vitamins and minerals are not essential to the longevity increasing and healthy lifestyle improving features of the present invention, on the margins they may provide additional benefit. For example A vitamins are supportive of vision and immune system operations and serves as a protectant against free radicals in general and reactive oxidative species in particular The anti-oxidation effects support mitochondrial and cellular integrity, health and functions. Various B vitamins serve as cofactors for several important enzymes including choline acetyltransferase and multiple enzymes of the citric acid cycle and electron trans chain. Vitamin c is another potent anti-oxidant that acts directly as an electron donor. Vitamin C is also an important cofactor for many hydroxylation enzymes. Vitamin D in its active form acts as a transcription factor, notably supporting synthesis of vitamin A metabolite receptors and synthesis of several hormone receptor proteins including androgen and estrogen receptors. Vitamin K is involved in several carboxylation reactions, including several involved in bone growth and maintenance and blood clotting. Vitamin K uptake may be improved when co-administered with the prohormone, rapamycin, CBD composition of the present invention. Selenium is an important co-factor for several thyroid hormone deiodinases and other enzymes and is essential to the GSH/GSSG anti-oxidant reactions. Magnesium is an important almost ubiquitous coenzyme supporting activities of over $10^2$ enzymes. Lithium is a modulator and stabilizer of membrane bound G-proteins and has both neuro-protective and intestinal barrier restorative functions. Manganese is a component in several metalloproteins and serves as a cofactor with oxidoreductases, transferases, hydrolases, lyases, isomerases, ligases, transcriptases, etc. It is probably best known for its presence in superoxide dismutase, an import protectant anti-oxidant enzyme. Zinc may be deficient in several identifiable at risk groups, including, but not limited to: lactating females, persons with sickle cell disease, vegetarians, etc. Zinc is an important cofactor across a wide variety of enzymes including some involved in intestinal health. Phosphorus is an important element in body structure such as bone. It is also important in control-activation/deactivation- of many enzymes by phosphorylation. Iron is important for safely binding oxygen in hemoglobin and myoglobin, but its ease in oxidation/reduction reactions, iron is integral in electron transfer functions involving, e.g., NADH dehydrogenase, coenzyme Q, cytochrome C, and Complex I and Complex II in the mitochondria. Potassium has many functions including, but not limited to: controlling membrane electrical potential and activity and as a PH adjuster across several cell membranes, including in the digestive system. While many individuals will be deficient in these vitamins, supplementing those who are deficient may support a higher base upon which the present invention can act to further improve.

A composition of the present invention may further comprise natural and/or artificial flavoring components, dyes or other coloring additives, preservatives and other conventional food supplement additives known in the art to increase palatability, storage options, etc.

The time and dosage amount administered will vary from and will be influenced by the age of the subject, and therefore may be adjusted. It is believed that generally, the younger the individual, the earlier results will be apparent with a smaller dosage amount needed to achieve optimal results. As the individual ages, the composition will have to be administered perhaps more frequently and in larger dosages for the individual to experience optimal results.

The form of the oral composition can be any suitable form that comprises the active ingredient and allows delivery to the select individual. An edible format is a preferred embodiment. Edibles can include substances designed to be swallowed and delivered to the gut through the throat and stomach. Alternative delivery embodiments including, but not limited to: lozenges, strips, drops, or other formats for buccal absorption; spray formats that may be delivered through an oral or nasal opening, a mist to be breathed into the body, a suppository, etc. CBD is absorbed across buccal and nasal membranes where it can render these membranes more receptive to absorbing other materials, e.g., a prohormone such as a DHEA or an antibiotic such as rapamycin.

As one example, a non-human animal preferably has been under a veterinarian's care and is general good health. However, this animal is aging and can benefit from receiving a therapeutic intervention that while not strictly necessary for life is beneficial to the animal and its human interactions though optimizing health, for example, by staving off or diminishing arthritis, other bone issues, such as dysplasia, lessening obesity problems and other issues seen in aging animals, such as diabetes, lethargy, pain, etc.

Cannabinoids may be used serially or coincident with corticosteroid or mitochondrial augmentation or rebalancing. Preferable embodiments comprise a blend of prohormone and rapamycin encase in a CBD jacket. A mixture with CBD as the major constituent can effectively "jacket" the other two components by surrounding the granules or molecules of each in the resultant agglomeration. The skilled artisan will be cognizant of the cannabinoid involvement in corticosteroid synthesis and release. When administration of one class is varied, the other classes may benefit from dosage or timing adjustment.

EXAMPLE 1

Rapamycin and DHEA are prepared as gelatinous microspheres. The microspheric particles are ejected into a heated stream of CBD in a chamber where the microspheres are allowed to cool so that the CBD solidifies. The microspheres are collected from the chamber bottom and packaged into a selected food or supplement, e.g., a gummi of desired shape, a chewing gum, etc.

EXAMPLE 2

Rapamycin and DHEA are present in in a preparation of liquefied CBD. CBD can be liquefied by melting in a heated chamber. The mixture is atomized by spraying into an atomization chamber where an air current cools the stream and forms microsphere particles of CBD, rapamycin and DHEA. Alternatively, a solvent may dissolve with CBD to maintain a liquid preparation. The liquid with DHEA, rapamycin and CBD with solvent is atomized by spraying into a stream of heated gas, e.g., hot air or nitrogen. The atomization forms small droplets whose solvent is evaporated while passing through the stream of hot air. Microsphere particles are collected after passing through the evaporative stream.

Modification of these exemplary microsphere forming practices or other microsphere formation methods are capable of forming the preferred microspheric embodiments of the present invention.

EXAMPLE 3

In an animal study, a five year old canine (age dependent on the breed, the animal size, etc.) is evaluated at its annual visit. This visit includes a hormonal profile as well as questioning the dog owner about the animal's activities and general health. The veterinarian observes that is common at this age for this type of dog, testosterone levels are continuing to drop and that the dog might benefit from restoring circulating levels of testosterone or other androgenic hormone in the blood.

The veterinarian calculates a target testosterone level and suggests simple oral supplements of DHEA that can help the dog achieve these levels and to thereby pep up the dog to increase enjoyment of the dog and human associates. The prohormone is co-administered with longevity supporting rapamycin and a cannabinoid, e.g., cannabidiol, in a chicken flavored gummi. This format includes CBD that facilitates uptake of both other compounds in the gut and results in more predictable outcomes.

Gummis of different formulation may be shape or color coded to allow the dispensing person to modify amounts and groups of compounds delivered in accordance with instructions or personal preferences. For example, a red gummi may include generally recommended amounts of: vitamin A carotenoids, B1 thiamin, B2 riboflavin, B3 niacin, B5 panthenic acid, B6, pyridoxal, B7 biotin, B9 folic acid/folate, B12 cobalamin, C ascorbate/ascorbic acid, D2 ergocalciferol, D3 cholcalciferol, K1 phylloquinone, K2 menaquinone, retinol, and/or retinyl ester. A green gummi may include: selenium, lithium, potassium, iron, phosphorus, zinc, manganese, and/or magnesium in conjunction with androgenic prohormone, rapamycin, and one or more cannabinoid compounds that bind and stimulate a mammalian endocannabinoid receptor. These are just examples. Other examples might be a teal gummi pill comprising: B1, B2, B3, B9, B12, Mg, and prohormone. Different formulations may be arbitrarily selected and distinguished for each gummi set to allow dosage personalized dosing. Though rare, when formulating the gummis attention should be paid to avoiding clumping or other undesired interactions between components.

Concluding Comments

Combined interventions involving two or more episodes of redirecting/rebalancing immune/allergy activity, balancing androgen levels in circulation, improving animal activity and outlook by optimizing mitochondrial activities will allow even more robust human-animal interaction and better outcomes for the participants. Mitochondrial activities may also be improved though supplementation with rapamycin and the CBD cannabinolic component in the composition of the invention. CBD has multiple effects, including, but not limited to: stimulating appetite, supporting mitochondrial activity, and enhancing intestinal uptake of the rapamycin and prohormone.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting. Although for simplicity in drafting the claims below are drafted in a manner where each dependent claim specifically asserts dependent status with only a single claim, the reader is put on notice that for purpose of disclosure every claim that references a preceding claim also implicitly is understood to have alternate dependency to all claims ultimately depending from the same claim or claims.

Examples useful in practicing this invention may include a composition or using a composition that improves a non-human animal's well-being that may include, contain or comprise an orally or subcutaneously administrable substance having at least one dosage selected from the group consisting of: a mitochondrial booster, an androgen hormone and a prohormone, said dosage selected to optimize at least one physiologic function in a selected mammal. Examples may further feature a compound that has or supports cannabinolic activity perhaps with presence of an endocannabinoid substance. Activity of such compound may be effected through a G-protein coupled receptor such as $CB_1$, $CB_2$, $TRPV_1$, $TRPV_2$, $TRPV_3$, $TRPV_4$, $TRPA_1$, $TRPM_8$, $GPR_{18}$, $GPR_{55}$, $GPR_{118}$, and/or $GPR_{119}$. Anti-oxidant activity may be featured in one or more or the constituents formulated into the product composition.

Cannabinolic activity may reside in, for example, an endogenous mammalian cannabinoid, a phytocannabinoid and/or a synthetic cannabinoid including but not limited to: AEA, 2AG, PEA, OEA, LEA, URB597, URB937, AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, Cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A, KML29, MAFP, MJN110, ML30, N-arachidonoyl maleimide, OL-135, OL92, PF-04457845, SA-57, ST4070, URB880, URB937, indomethacin, MK-886, resveratrol, cis-resveratrol, aspirin, COX-1 inhibitor II, loganin, tenidap, SC560, FR 122047 hydrochloride, valeryl salicylate, FR122047 hydrate, ibuprofen, TFAP, 6-methoxy-2-naphthylacetic acid, meloxicam, APHS, etodolac, meloxicam, meloxicam sodium salt, N-(4-acetamidophenyl)indomethacin amide, N-(2-phenylethyl)indomethacin amide, N-(3-pyridyl)indomethacin amide, indomethacin heptyl ester, SC236, sulinac, sulindac sulfide, pravadoline, naproxen, naproxen sodium salt, meclofenamate sodium, ibuprofen, S-ibuprofen, piroxicam, ketoprofen, S-ketoprofen, R-ibuprofen, Ebselen, ETYA, diclofenac, diclofenac diethylamine, flurbiprofen, fexofenadine, Pterostilbene, Pterocarpus marsupium, 9,12-octadecadiynoic acid, Ketorolac (tromethamine salt), NO-indomethacin, S-flurbiprofen, sedanolide, green tea extract (e.g., epicatechin), licofelone, lornoxicam, rac ibuprofen-d3, ampirxicam, zaltoprofen, 7-(trifluoromethyl)1H-indole-2,3-dione, aceclofenac, acetylsalicylic acid-d4, S-ibuprofen lysinate, loxoprofen, CAY10589, ZLJ-6, isoicam, dipyrone, YS121, MEG (mercaptoethylguanidine), etc.

Such cannabinoids may be identified as members of a class such as: cannabigerol class, cannabichromene class, cannabicyclol class, $\Delta^8$-tetrahydrocannabinol class, cannabieson class, cannabinol and cannabinodiol class, cannabitriol class and miscellaneous class.

Popular compositions used to practice the invention may include one or more cannabinoids selected from the group consisting of: CBGA, CBGAM, CBG, CBGM; CBGVA, CBGV, CBCA, CBC, CBCVA, CBCV, CBDA, CBD, CBDM, CBD-C4, CBDVA, CBDV, CBD-C1, THCA-A, THCA-B, 6a,10a-trans-6a,7,8,10a-tetra hydro-6,6,9-trimethyl-3-pentyl-6H-dibenzo[b,d]pyran-1-ol, THC,) THCA-C4, THC-C4, THCVA, THCV, $\Delta^7$-cis-isotetrahydrocannabivarin, THCA-C1, THC-C1, $\Delta^8$-TCA, $\Delta^8$-THC, CBL, CBLA, CBLV, CBEA-A, CBEA-B, CBE, CBNA, CBN, CBNM, CBN-C4, CBV, CBN-C2, CBN-C1), CBND, CBDV, CBT, 10-EHDT, 8,9-DHDT, CBTV, CBTVE, DCBF, CBF, CBCN, CBT, OTHC, cis-THC, 2H-iso-HHCV, CBR and triOH-THC.

Some practices of the invention can feature metabolism directive or accessory compounds or metabolically active compounds including, but not limited to: an FAAH inhibitor, R-WIN 55,212-2, a MAGL inhibitor, an EFA, oxytocin, ω-3 fatty acid, ω-6 fatty acid.

Some formulations may feature, for example, N-alkylamides, phytoalkanes, n-alkanes, N-acylethanolamines, flavonoids, curcuminoids, polyphenols, biphenyl neolignans, sesquiterpenes, N-Isobutylamides and/or p-hydroxyphenyl-O-arylcarba mates, whose carbon presence in the molecule of interest may be specific or in a range where each molecule comprises from 9 to 39 carbon atoms, for example, 9, 10, 11, 12, 13, 14,15,16,17, 18, 19, 20, 21, 22,23, 24, 25,26,27, 28, 29, 30, 31, 32, 33, 34, 35, 36, 37, 38 and/or 39 C/molecule.

Carbon chains may include branches with preferred compounds expected to feature 2-methyl-, 3-methyl-, and dimethyl attachments. Nonacosane, heptacosane, 2,6-dimethyl-tetra-decane, pentacosane, hexacosane, and hentriacontane are examples of useful carbon chains.

Phyto molecules are featured in some embodiments of this invention. A composition may thus feature parts or extracts, for example, of one of more sources derived from *Echinacea, Echinacea purpurea, Echinacea angustifolia*, curcurmin, *Salvia divinorum*, sage, lemon grass, hops, verbana, *Cannabis*, thyme, mango, *Helichrysum umbraculigerum*, liverwort, cacao, ginger, tumeric, *Curcuma longa, Magnolia officinalis*, Norway spruce, basil, *Myristica fragrans*, cloves, *Sciadopitys verticillata*, oregano, cinnamon, black pepper, hemp, rosemary, flax, *Elettaria repens*, etc.

Phyto- or phyto-mimic compounds/molecules may include but are not limited to: abinene, α-pinene, 4,8-dimethyl-1,7-nonadien-4-ol, 2-hydroxy-4-methyl-valeric, acid, methyl, ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, β-citral, guanidine, geraniol, bornyl, acetate, β-pinene, thymol, geranic, acid, methyl, ester, α-terpinyl, acetate, d-limonene, eugenol, geranyl, acetate, dihydrocarvyl, acetate, α-ylangene, cis-dodec-5-enal, 3-phenyl-2-propenoic, acid, methyl, ester, β-elemene, c, vanillin, epoxy-α-terpenyl, acetate, butanoic, acid, 2-methyl-, 3,7-dimethyl-2,6-octadienyl, ester, 1-methyl-4-(1-acetoxy-1-methylethyl)-cyclohex-2-enol, 1,2,3,4,4a,5,6,8a-octahydro-4a,8-dimethyl-2-(1-methylethenyl)-, [2r-(2à,4aà,8aá)]-naphthalene, p-mentha-1(7), 8-dien-2-ol, ç-muurolene, hydroxy-α-terpenyl, acetate, nerolidol, geranyl, bromide, (−)-α-panasinsen, pyrocatechol, ç-elemene, 9,10-dehydroisolongifolene, à-calacorene, cis-verbenol, acetic, acid, 1-methyl-1-(4-methyl-5-oxo-cyclohex-3-enyl)ethyl, ester, alloaromadendrene, z,z-2,6-dimethyl-3,5,7-octatriene-2-ol, 4-epi-cubedol, 2-oxabicyclo[2.2.2]octan-6-ol, 1,3,3-trimethyl-acetate, patchoulane, farnesol, caryophyllene, oxide, cis-lanceol, ledene, oxide-(ii), farnesol, acetate, 6-epi-shyobunol, falcarinol, phytol, aromadendrene, oxide-(2), heptacosane, longipinene, epoxide, hentriacontane, decamethyl-cyclopentasiloxane, geranyl, isobutyr, hexamethyl-cyclotrisiloxane, 1-docosene, tetratetracontane, dodecamethyl-cyclohexasiloxane, etc.

Supplemental components used to modify or to improve more rudimentary formulations or compositions may comprise, but are not limited to: β-caryophellene, a β-caryophyllene oxide, salvinorin A, myrcene, perrottetinenic acid, apigenin, quercetin, cannflavin A, cannflavin B, β-sitosterol, vitexin, isovitexin, kaempferol, luteolin, orientin, a gingerol, capsaicin, curcumin, demethoxycurcumin, bisdemethoxycurcumin, cyclocurcumin, trans-resveratrol, diferuloylmethane, trans-arachidins, trans-piceatannol, isoprenylated trans-resveratrol derivatives, sciadonic acid magnolol, honokiol, malyngamide B, (+) sabinene, (−) sabinene, lsobutylamide, dodeca-2E,4E-dienoic acid isobutylamide, dodeca-2E,4E, 8Z,10Z-tetraenoic acid alkylamide, 1-[(2E,4E,8Z)-tetradecatrienoyl] piperidine, β-caryophyllene, ajulemic acid, etc.

Compositions are not limited to classic medicament shapes or formats. For example, a gel, a powder, a liquid, a food supplement, a moist food, a dry food, a solidified matrix, etc., may be used for delivery. A 3-D printer may be applied to control dosing of the featured components, e.g., a hormone or prohormone, Delayed-release shaped constructs, a chewable substance. One or more formats may feature a plurality of packagings, wherein at least a first packaging contains active ingredient for admixing to at least a second package contents.

The invention claimed is:

1. A composition comprising an androgenic prohormone, rapamycin, and a cannabinoid compound that binds and stimulates a human endocannabinoid receptor, metformin, and growth hormone, and at least one mineral selected from the group consisting of: selenium, lithium, potassium, iron, phosphorus, zinc, manganese, and magnesium.

2. The composition of claim 1 wherein said endogenous endo-cannabinoid receptor is selected from the group consisting of: CB1, CB2, TRPV1, TRPV2, TRPV3, TRPV4, TRPA1, TRPM8, GPR119, GPR55, GPR118, and GPR18.

3. The composition of claim 2 wherein said cannabinoid compound also binds and stimulates at least one 5-HT receptor.

4. The composition of claim 1 wherein said cannabinoid compound comprises cannabidiol (CBD).

5. The composition of claim 1 further comprising an oil selected from the group consisting of: vegetable, rapeseed/canola, soy, corn, peppermint, lavender, sandalwood, bergamot, rose, chamomile, ylang-ylang, tea tree, myrcene/hops, jasmine, and lemon.

6. The composition of claim 1 further comprising nutmeg or nutmeg extract.

7. The composition of claim 1 present in an edible selected from the group consisting of: a toothpaste, a food formulation, a food supplement, a gummi, a prescription food product, a capsule, a pill, a spray, an ampule, and a chewing gum.

8. A gummi food comprising the composition of claim 1.

9. A chewing gum comprising the composition of claim 1.

10. The composition of claim 1 present in a format selected from the group consisting of: a liquid for spritzing into an oral or nasal opening, a liquid for misting, a liquid for sub cutaneous injection, a liquid for intra-venous injection, a liquid for intra-muscular injection, a lozenge, a buccal strip, and a suppository.

11. The composition of claim 10 present in a device comprising a mask or a tube that can deliver said liquid for misting into a nasal passage.

12. The composition of claim 1 present in a sterile format capable of presence in a syringe for injection.

13. The composition of claim 12, in a concentrated format designed for dilution prior to injection.

14. The composition of claim 1 further comprising at least one vitamin selected from the group consisting of: vitamin A carotenoids, B1 thiamin, B2 riboflavin, B3 niacin, B5 panthenic acid, B6, pyridoxal, B7 biotin, B9 folic acid/folate, B12 cobalamin, C ascorbate/ascorbic acid, D2 ergocalciferol, D3 cholcalciferol, K1 phylloquinone, K2 menaquinone, retinol, and retinyl ester.

15. The composition of claim 14 further comprising at least one mineral selected from the group consisting of: selenium, lithium, potassium, iron, phosphorus, zinc, manganese, and magnesium.

16. The composition of claim 1 further comprising at least one mineral selected from the group consisting of: selenium, lithium, potassium, iron, phosphorus, zinc, manganese, and magnesium.

17. The composition of claim 1 wherein said prohormone is selected from the group consisting of: DHEA, 7-keto DHEA and DHEA-S.

18. A method for providing a safe therapeutic composition to a human, said method comprising delivering to said human a composition comprising an androgenic prohormone, rapamycin, and a cannabinoid compound that binds and stimulates a human endocannabinoid receptor, metformin, and growth hormone, and at least one mineral selected from the group consisting of: selenium, lithium, potassium, iron, phosphorus, zinc, manganese, and magnesium.

19. The method of claim 18, further comprising prior to said delivering: a purging comprising introducing into said human an activated charcoal substance at a dosage level between ~500 mg/kg and ~2000 mg/kg.

20. The method of claim 19 wherein said activated charcoal is introduced as an oral presentation in solid format or aqueous suspension format.

21. The method of claim 19 wherein said activated charcoal substance comprises KUARAY®.

22. The method of claim 19 wherein said composition further comprises at least one vitamin selected from the group consisting of: vitamin A carotenoids, B1 thiamin, B2 riboflavin, B3 niacin, B5 panthenic acid, B6, pyridoxal, B7 biotin, B9 folic acid/folate, B12 cobalamin, C ascorbate/ascorbic acid, D2 ergocalciferol, D3 cholcalciferol, K1 phylloquinone, K2 menaquinone, retinol, and retinyl ester.

23. The method of claim 22 wherein said composition comprises: selenium, lithium, potassium, iron, phosphorus, zinc, manganese, and magnesium.

24. The method of claim 23 wherein said composition further comprises: vitamin A carotenoids, B1 thiamin, B2 riboflavin, B3 niacin, B5 panthenic acid, B6, pyridoxal, B7 biotin, B9 folic acid/folate, B12 cobalamin, C ascorbate/ascorbic acid, D2 ergocalciferol, D3 cholcalciferol, K1 phylloquinone, K2 menaquinone, retinol, and retinyl ester.

25. The method of claim 19 wherein said composition further comprises at least one mineral selected from the group consisting of: selenium, lithium, potassium, iron, phosphorus, zinc, manganese, and magnesium.

26. The method of claim 25 wherein said composition comprises: selenium, lithium, potassium, iron, phosphorus, zinc, manganese, and magnesium.

* * * * *